US006634363B1

(12) United States Patent
Danek et al.

(10) Patent No.: US 6,634,363 B1
(45) Date of Patent: Oct. 21, 2003

(54) METHODS OF TREATING LUNGS HAVING REVERSIBLE OBSTRUCTIVE PULMONARY DISEASE

(75) Inventors: Christopher James Danek, Santa Clara, CA (US); Michael Biggs, San Francisco, CA (US); Bryan Loomas, Los Gatos, CA (US); Michael D. Laufer, Menlo Park, CA (US); Gary Kaplan, San Francisco, CA (US); Kelly Shriner, Sunnyvale, CA (US)

(73) Assignee: Broncus Technologies, Inc., Mountain View, CA (US)

( * ) Notice: Subject to any disclaimer, the term of this patent is extended or adjusted under 35 U.S.C. 154(b) by 0 days.

(21) Appl. No.: 09/535,856

(22) Filed: Mar. 27, 2000

Related U.S. Application Data

(63) Continuation-in-part of application No. 09/296,040, filed on Apr. 21, 1999, now Pat. No. 6,411,852, which is a continuation-in-part of application No. 09/095,323, filed on Jun. 10, 1998, application No. 09/535,856, which is a continuation-in-part of application No. 09/436,455, filed on Nov. 8, 1999, which is a continuation-in-part of application No. 09/095,323, filed on Jun. 10, 1998, and a continuation-in-part of application No. 09/349,715, filed on Jul. 8, 1999, now Pat. No. 6,488,673, which is a continuation-in-part of application No. 08/994,064, filed on Dec. 19, 1997, now Pat. No. 6,083,255, which is a continuation-in-part of application No. 08/833,550, filed on Apr. 7, 1997, now Pat. No. 6,273,907.

(51) Int. Cl.[7] ............................................. A61B 19/00
(52) U.S. Cl. ....................................................... 128/898
(58) Field of Search .......................................... 128/898

(56) References Cited

U.S. PATENT DOCUMENTS

| 1,155,169 A | 9/1915 | Starkweather |
| 1,207,479 A | 12/1916 | Bisgaard |
| 2,072,346 A | 3/1937 | Smith |
| 3,568,659 A | 3/1971 | Karnegis |
| 3,692,029 A | 9/1972 | Adair |
| 4,522,212 A | 6/1985 | Gelinas et al. |

(List continued on next page.)

FOREIGN PATENT DOCUMENTS

| EP | 0 908 150 A1 | 4/1999 |
| EP | 0 908 713 A1 | 4/1999 |
| EP | 0 908 713 | 4/1999 |
| FR | 2659240 | 9/1991 |
| WO | WO 98/44854 A1 | 10/1998 |
| WO | WO 98/56234 A1 | 12/1998 |
| WO | WO 98/56324 A1 | 12/1998 |
| WO | WO 98/58681 A2 | 12/1998 |
| WO | WO 99/03413 A1 | 1/1999 |
| WO | WO 99/13779 A2 A3 | 3/1999 |
| WO | WO 99/34741 A1 | 7/1999 |
| WO | WO 99/44506 A1 | 9/1999 |
| WO | WO 99/45855 A1 | 9/1999 |
| WO | WO 00/51510 A1 | 9/2000 |
| WO | WO 01/03642 A1 | 1/2001 |

OTHER PUBLICATIONS

Hogg, J.C. (Oct. 1997). "The Pathology of Asthma," *APMIS*, 105(10)735–745.

Johnson, S. R. and Knox, A. J. (Aug. 1997). "Synthetic Functions of Airway Smooth Muscle in Asthma," *Trends. Pharmacol. Sci.* 18(8):288–292. (Review).

(List continued on next page.)

*Primary Examiner*—Corrine McDermott
*Assistant Examiner*—William H. Matthews
(74) *Attorney, Agent, or Firm*—Sanjay S. Bagade

(57) ABSTRACT

This relates to treating a lung having at least one symptom of reversible obstructive pulmonary disease, and more particularly, relates to advancing a treatment device into the lung and treating the lung with the device to at least reduce the ability of the lung to produce at least one of the symptoms of reversible obstructive pulmonary disease. This also includes additional steps that reduce the ability of the lung to produce at least one of the symptoms of reversible obstructive pulmonary disease and to reduce the resistance to the flow of air through a lung.

77 Claims, 2 Drawing Sheets

U.S. PATENT DOCUMENTS

| | | |
|---|---|---|
| 4,565,200 A | 1/1986 | Cosman |
| 4,584,998 A | 4/1986 | McGrail |
| 4,612,934 A | 9/1986 | Borkan |
| 4,674,497 A | 6/1987 | Ogasawara |
| 4,706,688 A | 11/1987 | Don Michael et al. |
| 4,709,698 A | 12/1987 | Johnston et al. |
| 4,790,305 A * | 12/1988 | Zoltan et al. .......... 128/200.23 |
| 4,802,492 A | 2/1989 | Grunstein |
| 4,827,935 A | 5/1989 | Geddes et al. |
| 4,862,886 A | 9/1989 | Clarke et al. |
| 4,920,978 A | 5/1990 | Colvin |
| 4,955,377 A | 9/1990 | Lennox et al. |
| 4,976,709 A | 12/1990 | Sand |
| 5,019,075 A | 5/1991 | Spears et al. |
| 5,053,033 A | 10/1991 | Clarke |
| 5,056,519 A | 10/1991 | Vince |
| 5,084,044 A | 1/1992 | Quint |
| 5,096,916 A | 3/1992 | Skupin |
| 5,100,388 A | 3/1992 | Behl et al. |
| 5,100,423 A | 3/1992 | Fearnot |
| 5,103,804 A | 4/1992 | Abele et al. |
| 5,107,830 A * | 4/1992 | Younes .................. 128/204.18 |
| 5,116,864 A | 5/1992 | March et al. |
| 5,117,828 A | 6/1992 | Metzger et al. |
| 5,135,517 A | 8/1992 | McCoy |
| 5,170,803 A | 12/1992 | Hewson et al. |
| 5,174,288 A | 12/1992 | Bardy et al. |
| 5,191,883 A | 3/1993 | Lennox et al. |
| 5,215,103 A | 6/1993 | Desai |
| 5,255,678 A | 10/1993 | Deslauriers et al. |
| 5,255,679 A | 10/1993 | Imran |
| 5,265,604 A | 11/1993 | Vince |
| 5,281,218 A | 1/1994 | Imran |
| 5,293,869 A | 3/1994 | Edwards et al. |
| 5,309,910 A | 5/1994 | Edwards et al. |
| 5,313,943 A | 5/1994 | Houser et al. |
| 5,345,936 A | 9/1994 | Pomeranz et al. |
| 5,368,591 A | 11/1994 | Lennox et al. |
| 5,370,679 A | 12/1994 | Atlee, III |
| 5,374,287 A | 12/1994 | Rubin |
| 5,383,917 A | 1/1995 | Desai et al. |
| 5,394,880 A | 3/1995 | Atlee, III |
| 5,396,887 A | 3/1995 | Imran |
| 5,400,783 A | 3/1995 | Pomeranz et al. |
| 5,411,025 A | 5/1995 | Webster, Jr. |
| 5,415,166 A | 5/1995 | Imran |
| 5,415,656 A | 5/1995 | Tihon et al. |
| 5,417,687 A | 5/1995 | Nardella et al. |
| 5,423,744 A | 6/1995 | Gencheff et al. |
| 5,423,811 A | 6/1995 | Imran et al. |
| 5,431,696 A | 7/1995 | Atlee, III |
| 5,433,730 A | 7/1995 | Alt |
| 5,443,470 A | 8/1995 | Stern et al. |
| 5,454,782 A | 10/1995 | Perkins |
| 5,456,667 A | 10/1995 | Ham et al. |
| 5,458,596 A | 10/1995 | Lax et al. |
| 5,465,717 A | 11/1995 | Imran et al. |
| 5,471,982 A | 12/1995 | Edwards et al. |
| 5,496,311 A | 3/1996 | Abele et al. |
| 5,500,011 A | 3/1996 | Desai |
| 5,505,728 A | 4/1996 | Ellman et al. |
| 5,509,419 A | 4/1996 | Edwards et al. |
| 5,522,862 A | 6/1996 | Testerman et al. |
| 5,531,779 A | 7/1996 | Dahl et al. |
| 5,540,681 A | 7/1996 | Strul et al. |
| 5,545,161 A | 8/1996 | Imran |
| 5,545,193 A | 8/1996 | Fleischman et al. |
| 5,549,559 A | 8/1996 | Eshel |
| 5,549,655 A | 8/1996 | Erickson |
| RE35,330 E | 9/1996 | Malone et al. |
| 5,558,073 A | 9/1996 | Pomeranz et al. |
| 5,562,608 A | 10/1996 | Sekins et al. |
| 5,588,432 A | 12/1996 | Crowley |
| 5,595,183 A | 1/1997 | Swanson et al. |
| 5,598,848 A | 2/1997 | Swanson et al. |
| 5,601,088 A | 2/1997 | Swanson et al. |
| 5,605,157 A | 2/1997 | Panescu et al. |
| 5,607,419 A | 3/1997 | Amplatz et al. |
| 5,607,462 A | 3/1997 | Imran |
| 5,620,438 A | 4/1997 | Amplatz et al. |
| 5,624,439 A | 4/1997 | Edwards et al. |
| 5,626,618 A | 5/1997 | Ward et al. |
| 5,630,425 A | 5/1997 | Panescu et al. |
| 5,634,471 A | 6/1997 | Fairfax et al. |
| 5,678,535 A | 10/1997 | DiMarco |
| 5,680,860 A | 10/1997 | Imran |
| 5,681,308 A | 10/1997 | Edwards et al. |
| 5,693,078 A | 12/1997 | Desai et al. |
| 5,699,799 A | 12/1997 | Xu et al. |
| 5,707,352 A | 1/1998 | Sekins et al. |
| 5,722,401 A | 3/1998 | Pietroski et al. |
| 5,722,403 A | 3/1998 | McGee et al. |
| 5,722,416 A | 3/1998 | Swanson et al. |
| 5,730,128 A | 3/1998 | Pomeranz et al. |
| 5,730,726 A | 3/1998 | Klingenstein |
| 5,730,741 A | 3/1998 | Horzewski et al. |
| 5,740,808 A | 4/1998 | Panescu et al. |
| 5,752,518 A | 5/1998 | McGee et al. |
| 5,755,753 A | 5/1998 | Knowlton |
| 5,759,158 A | 6/1998 | Swanson |
| 5,769,846 A | 6/1998 | Edwards et al. |
| 5,772,590 A | 6/1998 | Webster, Jr. |
| 5,779,698 A | 7/1998 | Clayman et al. |
| 5,782,239 A | 7/1998 | Webster, Jr. |
| 5,782,899 A | 7/1998 | Imran |
| 5,792,064 A | 8/1998 | Panescu et al. |
| 5,795,303 A | 8/1998 | Swanson et al. |
| 5,807,306 A | 9/1998 | Shapland et al. |
| 5,810,807 A | 9/1998 | Ganz et al. |
| 5,827,277 A | 10/1998 | Edwards |
| 5,836,947 A | 11/1998 | Fleischman et al. |
| 5,843,075 A | 12/1998 | Taylor |
| 5,843,077 A | 12/1998 | Edwards |
| 5,846,238 A | 12/1998 | Jackson et al. |
| 5,848,969 A | 12/1998 | Panescu et al. |
| 5,848,972 A | 12/1998 | Triedman et al. |
| 5,855,577 A | 1/1999 | Murphy-Chutorian et al. |
| 5,860,974 A | 1/1999 | Abele |
| 5,863,291 A | 1/1999 | Schaer |
| 5,865,791 A | 2/1999 | Whayne et al. |
| 5,868,740 A | 2/1999 | LeVeen et al. |
| 5,871,443 A | 2/1999 | Edwards et al. |
| 5,871,523 A | 2/1999 | Fleischman et al. |
| 5,873,865 A | 2/1999 | Horzewski et al. |
| 5,881,727 A | 3/1999 | Edwards |
| 5,882,346 A | 3/1999 | Pomeranz et al. |
| 5,891,136 A | 4/1999 | McGee et al. |
| 5,897,554 A | 4/1999 | Chia et al. |
| 5,904,651 A | 5/1999 | Swanson et al. |
| 5,904,711 A | 5/1999 | Flom et al. |
| 5,908,445 A | 6/1999 | Whayne et al. |
| 5,908,446 A | 6/1999 | Imran |
| 5,911,218 A | 6/1999 | DiMarco |
| 5,935,079 A | 8/1999 | Swanson et al. |
| 5,941,869 A | 8/1999 | Patterson et al. |
| 5,954,661 A | 9/1999 | Greenspon et al. |
| 5,954,662 A | 9/1999 | Swanson et al. |
| 5,957,961 A | 9/1999 | Maguire et al. |
| 5,964,753 A | 10/1999 | Edwards |
| 5,964,796 A | 10/1999 | Imran |
| 5,971,983 A | 10/1999 | Lesh |

| | | |
|---|---|---|
| 5,972,026 A | 10/1999 | Laufer et al. |
| 5,979,456 A | 11/1999 | Magovern |
| 5,991,650 A | 11/1999 | Swanson et al. |
| 5,992,419 A | 11/1999 | Sterzer et al. |
| 5,993,462 A | 11/1999 | Pomeranz et al. |
| 5,999,855 A | 12/1999 | DiMarco |
| 6,004,269 A | 12/1999 | Crowley et al. |
| 6,009,877 A | 1/2000 | Edwards |
| 6,010,500 A | 1/2000 | Sherman et al. |
| 6,024,740 A | 2/2000 | Lesh et al. |
| 6,036,687 A | 3/2000 | Laufer et al. |
| 6,053,172 A | 4/2000 | Hovda et al. |
| 6,071,280 A | 6/2000 | Edwards et al. |
| 6,083,255 A | 7/2000 | Laufer et al. |
| 6,092,528 A | 7/2000 | Edwards |
| 6,142,993 A | 11/2000 | Whayne et al. |
| 6,200,333 B1 | 3/2001 | Laufer |
| 6,254,598 B1 | 7/2001 | Edwards et al. |
| 6,283,989 B1 | 9/2001 | Laufer et al. |
| 6,299,633 B1 | 10/2001 | Laufer |
| 6,411,852 B1 | 6/2002 | Danek et al. |

OTHER PUBLICATIONS

Macklem, P.T. (Jun. 1989). "Mechanical Factors Determining Maximum Bronchoconstriction," *Eur. Respir. J. Suppl.*, 6:516s–519s.

Netter, F. H. (1979). "Respiratory System: A Compilation of Paintings Depicting Anatomy and Embryology, Physiology, Pathology, Pathophysiology, and Clinical Features and Treatment of Diseases," *In The Ciba Collection of Medical Illustrations*. M. B. Divertie ed., Summit: New Jersey (7)119–135.

Wiggs, B.R. et al. (1997). "On the Mechanism of Mucosal Folding in Normal and Asthmatic Airways," *J. Appl. Physiol.* 83(6):1814–1821.

U.S. patent application Ser. No. 09/176,899, Laufer, filed Oct. 22, 1998.

U.S. patent application Ser. No. 09/244,173, Laufer et al., filed Feb. 4, 1999.

U.S. patent application Ser. No. 09/280,672, Laufer et al., filed Mar. 29, 1999.

Dierkesmann et al. (1990). "Indication and Results of Endobronchial Laser Therapy," *Lung* (Suppl.):1095–1102.

U.S. patent application Ser. No. 09/095,323, Laufer, filed Jun. 10, 1998.

U.S. patent application Ser. No. 09/296,040, Danek et al., filed Apr. 21, 1999.

U.S. patent application Ser. No. 09/349,715, Laufer et al., filed Jul. 8, 1999.

U.S. patent application Ser. No. 09/436,455, Danek et al., filed Nov. 8, 1999.

U.S. patent application Ser. No. 09/095,323, Laufer, filed Jun. 10, 1998.

U.S. patent application Ser. No. 09/244,173, Laufer et al., filed Feb. 4, 1999.

U.S. patent application Ser. No. 09/349,715, Laufer et al., filed Jul. 8, 1999.

Dierkesmann et al. (1990). "Indication and Results of Endobronchial Laser Therapy," *Lung* (Suppl.):1095–1102.

Hogg, J. C. (Oct. 1997). "The Pathology of Asthma," *APMIS*, 105(10)735–745.

Johnson, S. R. and Knox, A. J. (Aug. 1997). "Synthetic Functions of Airway Smooth Muscle in Asthma," *Trends. Pharmacol. Sci.* 18(8):288–292. (Review).

Macklem, P. T. (Jun. 1989). "Mechanical Factors Determining Maximum Bronchoconstriction," *Eur. Respir. J. Suppl.*, 6:516s–519s.

Netter, F. H. (1979). "Respiratory System: A Compilation of Paintings Depicting Anatomy and Embryology, Physiology, Pathology, Pathophysiology, and Clinical Features and Treatment of Diseases," *In The Ciba Collection of Medical Illustrations*. M. B. Divertie ed., Summit: New Jersey (7)119–135.

Wiggs, B. R. et al. (1997). "On the Mechanism of Mucosal Folding in Normal and Asthmatic Airways," *J. Appl. Physiol.* 83(6):1814–1821.

* cited by examiner

METHODS OF TREATING LUNGS HAVING REVERSIBLE OBSTRUCTIVE PULMONARY DISEASE

This is a Continuation-in-part application of U.S. application Ser. No. 09/296,040 filed Apr. 21, 1999, now U.S. Pat. No. 6,411,852, which is a Continuation-in-part of U.S. application Ser. No. 09/095,323 filed Jun. 10, 1998; this is also a Continuation-in-part application of U.S. application Ser. No. 09/436,455 filed Nov. 8, 1999 which is a Continuation-in-part of U.S. application Ser. No. 09/095,323 filed Jun. 10, 1998 and is also a Continuation-in-part of U.S. application Ser. No. 09/349,715 filed Jul. 8, 1999 now U.S. Pat. No. 6,488,673 which is a Continuation-in-part of U.S. application Ser. No. 08/994,064 filed Dec. 19, 1997, now U.S. Pat. No. 6,083,255, which is a Continuation-in-part of U.S. application Ser. No. 08/833,550, filed Apr. 7, 1997, now U.S. Pat. No. 6,273,907. All the above applications are incorporated by reference herein in their entirety.

BACKGROUND OF THE INVENTION

1. Field of the Invention

The invention relates to a method of treating a lung having at least one symptom of reversible obstructive pulmonary disease, and more particularly, the invention relates to advancing a treatment device into the lung and treating the lung with the device to at least reduce the ability of the lung to produce at least one of the symptoms of reversible obstructive pulmonary disease. The invention includes additional steps that reduce the ability of the lung to produce at least one of the symptoms of reversible obstructive pulmonary disease and to reduce the resistance to the flow of air through a lung.

2. Brief Description of the Related Art

Reversible obstructive pulmonary disease includes asthma and reversible aspects of chronic obstructive pulmonary disease (COPD). Asthma is a disease in which (i) bronchoconstriction, (ii) excessive mucus production, and (iii) inflammation and swelling of airways occur, causing widespread but variable airflow obstruction thereby making it difficult for the asthma sufferer to breathe. Asthma is a chronic disorder, primarily characterized by persistent airway inflammation. However, asthma is further characterized by acute episodes of additional airway narrowing via contraction of hyper-responsive airway smooth muscle.

The reversible aspects of COPD generally describe excessive mucus production in the bronchial tree. Usually, there is a general increase in bulk (hypertrophy) of the large bronchi and chronic inflammatory changes in the small airways. Excessive amounts of mucus are found in the airways and semisolid plugs of mucus may occlude some small bronchi. Also, the small airways are narrowed and show inflammatory changes. The reversible aspects of COPD include partial airway occlusion by excess secretions, and airway narrowing secondary to smooth muscle contraction, bronchial wall edema and inflation of the airways.

In asthma, chronic inflammatory processes in the airway play a central role in increasing the resistance to airflow within the lungs. Many cells and cellular elements are involved in the inflammatory process, particularly mast cells, eosinophils T lymphocytes, neutrophils, epithelial cells, and even airway smooth muscle itself. The reactions of these cells result in an associated increase in the existing sensitivity and hyper-responsiveness of the airway smooth muscle cells that line the airways to the particular stimuli involved.

The chronic nature of asthma can also lead to remodeling of the airway wall (i.e., structural changes such as thickening or edema) which can further affect the function of the airway wall and influence airway hyper-responsiveness. Other physiologic changes associated with asthma include excess mucus production, and if the asthma is severe, mucus plugging, as well as ongoing epithelial denudation and repair. Epithelial denudation exposes the underlying tissue to substances that would not normally come in contact with them, further reinforcing the cycle of cellular damage and inflammatory response.

In susceptible individuals, asthma symptoms include recurrent episodes of shortness of breath (dyspnea), wheezing, chest tightness, and cough. Currently, asthma is managed by a combination of stimulus avoidance and pharmacology.

Stimulus avoidance is accomplished via systematic identification and minimization of contact with each type of stimuli. It may, however, be impractical and not always helpful to avoid all potential stimuli.

Asthma is managed pharmacologically by: (1) long term control through use of anti-inflammatories and long-acting bronchodilators and (2) short term management of acute exacerbations through use of short-acting bronchodilators. Both of these approaches require repeated and regular use of the prescribed drugs. High doses of corticosteroid anti-inflammatory drugs can have serious side effects that require careful management. In addition, some patients are resistant to steroid treatment. The difficulty involved in patient compliance with pharmacologic management and the difficulty of avoiding stimulus that triggers asthma are common barriers to successful asthma management.

Asthma is a serious disease with growing numbers of sufferers. Current management techniques are neither completely successful nor free from side effects.

Accordingly, it would be desirable to provide an asthma treatment which improves airflow without the need for patient compliance.

In addition to the airways of the lungs, other body conduits such as the esophagus, ureter, urethra, and coronary arteries, are also subject to periodic reversible spasms that produce obstruction to flow.

SUMMARY OF THE INVENTION

The present invention relates to methods for treating a lung, preferably having at least one symptom of reversible obstructive pulmonary disease, comprising the steps of advancing a treatment device into the lung and treating the lung with the device to at least reduce the ability of the lung to produce at least one symptom of reversible obstructive pulmonary disease and to decrease the resistance to the flow of air through the lung.

A variation of the invention includes the method described above further comprising the step of locating one or more treatment sites within an airway of the lung, selecting at least one of the treatment sites and treating at least one of the treatment sites selected in the selecting step. The invention may further include performing the steps while the lung is experiencing at least one symptom of either natural or artificially induced reversible obstructive pulmonary disease.

A further variation of the invention includes the method described above and further includes the steps of testing the lung for at least one pre-treatment pulmonary function value prior to the treating step, and re-testing the lung for at least one post-treatment pulmonary function value subsequent to the treating step.

A further variation of the invention includes the method described above further comprising identifying treatment sites within the airway being highly susceptible to either airway inflammation, airway constriction, excessive mucus secretion, or any other symptom of reversible obstructive pulmonary disease.

Another variation of the invention includes the method described above and the additional step of stimulating the lung to produce at least one artificially induced symptom of reversible obstructive pulmonary disease. The invention may further comprise the step of evaluating the results of the stimulating step.

Another variation of the invention includes the method described above where treating at least airway tissue within the lung further comprises the step of determining the effect of the treatment by visually observing the airway for blanching of airway tissue.

Another variation of the invention includes the method described above where treating at least airway tissue at a treatment site within the lung further comprises the step of monitoring electrical impedance of tissue at one or more points.

Another variation of the invention includes the method described above where treating the lung includes submucosal treatment of at least airway tissue in the lung.

Another variation of the invention includes the method described above where the treating step includes treating the lung by depositing a radioactive substance in at least one treatment site within the lung.

Another variation of the invention include the method described above further including the step of scraping tissue from a wall of an airway within the lung prior to the treating step. The invention may further comprise depositing a substance on the scraped wall of the airway.

Another variation of the invention includes the method described above where the treating step uses a modality selected from the group consisting of mechanical, chemical, radio frequency, radioactive energy, heat, and ultrasound.

Another variation of the invention includes the method described above further comprising pre-treating the lung to at least reduce the ability of the lung to produce at least one symptom of reversible obstructive pulmonary disease prior to the treating step, where at least one parameter of the pre-treating step is lesser than at least one parameter of the treating step.

Another variation of the invention comprises the method described above where the treating step includes separating the treating step into stages to reduce the healing load on the lung. The separating step may comprise treating different regions of the lung at different times or dividing the number of treatment sites into a plurality of groups of treatment sites and treating each group at a different time.

Another variation of the invention includes the method described above further comprising sensing movement of the lung and repositioning the treatment device in response to said sensing step.

Another variation of the invention includes the method described above further comprising reducing the temperature of lung tissue adjacent to a treatment site.

Another variation of the invention includes the method described above further comprising the step of providing drug therapy, exercise therapy, respiratory therapy, and/or education on disease management techniques to further reduce the effects of reversible obstructive pulmonary disease.

The invention further includes the method for reversing a treatment to reduce the ability of the lung to produce at least one symptom of reversible obstructive pulmonary disease comprising the step of stimulating re-growth of smooth muscle tissue in the lung.

The invention further includes the method of evaluating an individual having reversible obstructive pulmonary disease as a candidate for a procedure to reduce the ability of the individual's lung to produce at least one reversible obstructive pulmonary disease symptom by treating an airway within the lung of the individual, the method comprising the steps of assessing the pulmonary condition of the individual, comparing the pulmonary condition to a corresponding predetermined state; and evaluating the individual based upon the comparing step. The method may additionally comprise the steps of performing pulmonary function tests on the individual to obtain at least one pulmonary function value, comparing the at least one pulmonary function value to a corresponding predetermined pulmonary function value, and evaluating the individual based upon the comparing step.

The invention further comprises a method of evaluating the effectiveness of a procedure to reduce the ability of lung to produce at least one symptom of reversible obstructive pulmonary disease previously performed on an individual having reversible obstructive pulmonary disease, the method comprising the steps of assessing the pulmonary condition of the individual, comparing the pulmonary condition to a corresponding predetermined state; and evaluating the effectiveness of the procedure based upon the comparing step. The method may additionally comprise the steps of performing pulmonary function tests on the individual to obtain at least one pulmonary function value, treating the lung to at least reduce the ability of the lung to produce at least one symptom of reversible obstructive pulmonary disease, performing post-procedure pulmonary function tests on the individual to obtain at least one post-procedure pulmonary function value; and comparing the pulmonary function value with the post-procedure pulmonary function value to determine the effect of the treating step.

BRIEF DESCRIPTION OF THE DRAWINGS

The invention will now be described in greater detail with reference to the various embodiments illustrated in the accompanying drawings.

DETAILED DESCRIPTION

Figure 1:
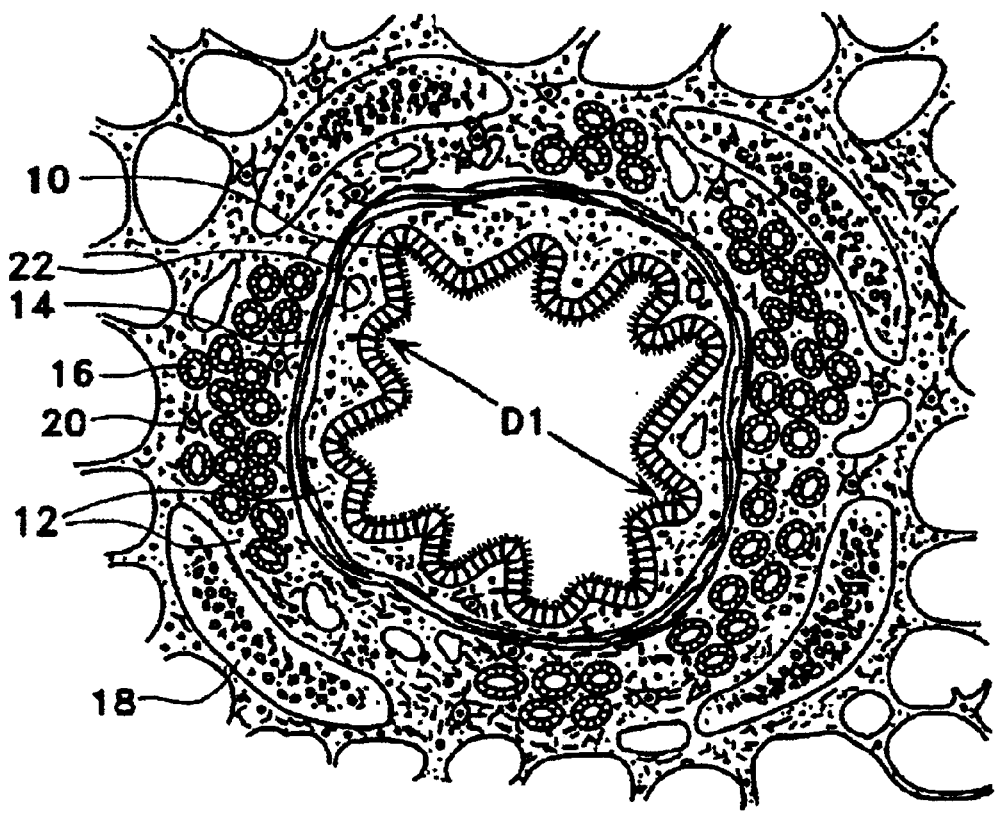
FIG. 1 is a cross sectional view of an airway in a healthy lung.

The invention relates to methods for improving airflow through the airways of a lung having reversible obstructive pulmonary disease. It is intended that the invention is applicable to any aspect of reversible obstructive pulmonary disease, including but not limited to asthma. One way of improving airflow is to decrease the resistance to airflow within the lungs. There are several approaches to reducing this resistance, including but not limited to reducing the ability of the airway to contract, increasing the airway diameter, reducing the inflammation of airway tissues, and/or reducing the amount of mucus plugging of the airway. The present invention includes advancing a treatment device into the lung and treating the lung to at least reduce the ability of the lung to produce at least one symptom of reversible obstructive pulmonary disease. The following is a brief discussion of some causes of increased resistance to airflow within the lungs and the inventive treatment of the invention described herein. As such, the following discussion is not intended to limit the aspects or objective of the inventive method as the inventive method may cause physiological changes not described below but such changes still contributing to reducing or eliminating at least one of the symptoms of reversible obstructive pulmonary disease.

Reducing the Ability of the Airway to Contract

The inventive treatment reduces the ability of the airways to narrow or to reduce in diameter due to airway smooth muscle contraction. The inventive treatment uses a modality of treatments including, but not limited to the following: chemical, radio frequency, radioactivity, heat, ultrasound, radiant, laser, microwave, or mechanical energy (such as in the form of cutting, punching, abrading, rubbing, or dilating). This treatment reduces the ability of the smooth muscle to contract thereby lessening the severity of an asthma attack. The reduction in the ability of the smooth muscle to contract may be achieved by treating the smooth muscle itself or by treating other tissues which in turn influence smooth muscle contraction or the response of the airway to the smooth muscle contraction. Treatment may also reduce airway responsiveness or the tendency of the airway to narrow or to constrict in response to a stimulus.

The amount of smooth muscle surrounding the airway can be reduced by exposing the smooth muscle to energy which either kills the muscle cells or prevents these cells from replicating. The reduction in smooth muscle reduces the ability of the smooth muscle to contract and to narrow the airway during a spasm. The reduction in smooth muscle and surrounding tissue has the added potential benefit of increasing the caliber or diameter of the airways, this benefit reduces the resistance to airflow through the airways. In addition to the use of debulking smooth muscle tissue to open up the airways, the device used in the present invention may also eliminate smooth muscle altogether by damaging or destroying the muscle. The elimination of the smooth muscle prevents the contraction or spasms of hyper-reactive airways of a patient having reversible obstructive pulmonary disease. By doing so, the elimination of the smooth muscle may reduce some symptoms of reversible obstructive pulmonary disease.

The ability of the airway to contract can also be altered by treatment of the smooth muscle in particular patterns. The smooth muscle is arranged around the airways in a generally helical pattern with pitch angles ranging from about −30 to about +30 degrees. Thus, the treatment of the smooth muscle in appropriate patterns interrupts or cuts through the helical pattern of the smooth muscle at a proper pitch and prevents the airway from constricting. This procedure of patterned treatment application eliminates contraction of the airways without completely eradicating smooth muscle and other airway tissue. A pattern for treatment may be chosen from a variety of patterns including longitudinal or axial stripes, circumferential bands, helical stripes, and the like as well as spot patterns having rectangular, elliptical, circular or other shapes. The size, number, and spacing of the treatment bands, stripes, or spots are chosen to provide a desired clinical effect of reduced airway responsiveness while limiting insult to the airway to a clinically acceptable level.

The patterned treatment of the tissues surrounding the airways with energy provides various advantages. The careful selection of the portion of the airway to be treated allows desired results to be achieved while reducing the total healing load. Patterned treatment can also achieve desired results with decreased morbidity, preservation of epithelium, and preservation of a continuous or near continuous ciliated inner surface of the airway for mucociliary clearance. The pattern of treatment may also be chosen to achieve desired results while limiting total treatment area and/or the number of airways treated, thereby improving speed and ease of treatment.

Application of energy to the tissue surrounding the airways may also cause the DNA of the cells to become cross linked. The treated cells with cross linked DNA are incapable of replicating. Accordingly, over time, as the smooth muscle cells die, the total thickness of smooth muscle decreases because of the inability of the cells to replicate. The programmed cell death causing a reduction in the volume of tissue is called apoptosis. This treatment does not cause an immediate effect but causes shrinking of the smooth muscle and opening of the airway over time and substantially prevents re-growth. The application of energy to the walls of the airway may also be used to cause a cross linking of the DNA of the mucus gland cells thereby preventing them from replicating and reducing excess mucus plugging or production over time.

The ability of the airways to contract may also be reduced by altering mechanical properties of the airway wall, such as by increasing stiffness of the wall or by increasing parenchymal tethering of the airway wall. Both of these methods increase the strength of the airway wall and further oppose contraction and narrowing of the airway.

There are several ways to increase the stiffness of the airway wall. One way to increase stiffness is to induce fibrosis or a wound healing response by causing trauma to the airway wall. The trauma can be caused by delivery of therapeutic energy to the tissue in the airway wall, by mechanical insult to the tissue, or by chemically affecting the tissue. The energy is preferably delivered in such a way that it minimizes or limits the intra-luminal thickening that may occur.

Another way to increase the effective stiffness of the airway wall is to alter the submucosal folding of the airway upon narrowing. The mucosal layer includes the epithelium, its basement membrane, and the lamina propria, a subepithelial collagen layer. The submucosal layer may also play a role in airway folding. As an airway narrows, its perimeter remains relatively constant, with the mucosal layer folding upon itself. As the airway narrows further, the mucosal folds mechanically interfere with each other, effectively stiffening the airway. In asthmatic patients, the number of folds is fewer and the size of the folds is larger, and thus, the airway is free to narrow with less mechanical interference of mucosal folds than in a healthy patient. Thus, asthmatic patients have a decrease in airway stiffness and the airways have less resistance to narrowing.

The mucosal folding in asthmatic patients can be improved by treatment of the airway in a manner which encourages folding. Preferably, a treatment will increase the number of folds and/or decrease the size of the folds in the mucosal layer. For example, treatment of the airway wall in a pattern such as longitudinal stripes can encourage greater number of smaller mucosal folds and increase airway stiffness.

The mucosal folding can also be increased by encouraging a greater number of smaller folds by reducing the thickness of the mucosa and/or submucosal layer. The decreased thickness of the mucosa or submucosa may be achieved by application of energy which either reduces the number of cells in the mucosa or submucosal layer or which prevents replication of the cells in the mucosa or submucosal layer. A thinner mucosa or submucosal layer will have an increased tendency to fold and increased mechanical stiffening caused by the folds.

Another way to reduce the ability of the airways to contract is to improve parenchymal tethering. The parenchyma surrounds airways and includes the alveolus and tissue connected to and surrounding the outer portion of the airway wall. The parenchyma includes the alveolus and tissue connected to and surrounding the cartilage that supports the larger airways. In a healthy patient, the parenchyma provides a tissue network which connects to and helps to support the airway. Edema or accumulation of fluid in lung tissue in patients with asthma or COPD is believed to decouple the airway from the parenchyma reducing the restraining force of the parenchyma which opposes airway constriction. Energy can be used to treat the parenchyma to reduce edema and/or improve parenchymal tethering.

In addition, the applied energy may be used to improve connection between the airway smooth muscle and submucosal layer to the surrounding cartilage, and to encourage wound healing, collagen deposition, and/or fibrosis in the tissue surrounding the airway to help support the airway and prevent airway contraction.

Increasing the Airway Diameter

Hypertrophy of smooth muscle, chronic inflammation of airway tissues, and general thickening of all parts of the airway wall can reduce the airway diameter in patients with reversible obstructive pulmonary, disease. Increasing the overall airway diameter using a variety of techniques can improve the passage of air through the airways. Application of energy to the airway smooth muscle of an asthmatic patient can debulk or reduce the volume of smooth muscle. This reduced volume of smooth muscle increases the airway diameter for improved air exchange.

Reducing inflammation and edema of the tissue surrounding the airway can also increase the diameter of an airway. Inflammation and edema (accumulation of fluid) of the airway are chronic features of asthma. The inflammation and edema can be reduced by application of energy to stimulate wound healing and regenerate normal tissue. Healing of the epithelium or sections of the epithelium experiencing ongoing denudation and renewal allows regeneration of healthy epithelium with less associated airway inflammation. The less inflamed airway has an increased airway diameter both at a resting state and in constriction. The wound healing can also deposit collagen which improves parenchymal tethering.

Inflammatory mediators released by tissue in the airway wall may serve as a stimulus for airway smooth muscle contraction. Therapy that reduces the production and release of inflammatory mediator can reduce smooth muscle contraction, inflammation of the airways, and edema. Examples of inflammatory mediators are cytokines, chemokines, and histamine. The tissues which produce and release inflammatory mediators include airway smooth muscle, epithelium, and mast cells. Treatment of these structures with energy can reduce the ability of the airway structures to produce or release inflammatory mediators. The reduction in released inflammatory mediators will reduce chronic inflammation, thereby increasing the airway inner diameter, and may also reduce hyper-responsiveness of the airway smooth muscle.

A further process for increasing the airway diameter is by denervation. A resting tone of smooth muscle is nerve regulated by release of catecholamines. Thus, by damaging or eliminating nerve tissue in the airways the resting tone of the smooth muscle is reduced, and the airway diameter is increased. Resting tone may also be reduced by directly affecting the ability of smooth muscle tissue to contract.

Reducing Plugging of the Airway

Excess mucus production and mucus plugging are common problems during both acute asthma exacerbation and in chronic asthma management. Excess mucus in the airways increases the resistance to airflow through the airways by physically blocking all or part of the airway. Excess mucus may also contribute to increased numbers of leukocytes found in airways of asthmatic patients by trapping leukocytes. Thus, excess mucus can increase chronic inflammation of the airways.

One type of asthma therapy involves treatment of the airways with energy to target and reduce the amount of mucus producing cells and glands and to reduce the effectiveness of the remaining mucus producing cells and glands. The treatment can eliminate all or a portion of the mucus producing cells and glands, can prevent the cells from replicating or can inhibit their ability to secrete mucus. This treatment will have both chronic benefits in increasing airflow through the airways and will lessen the severity of acute exacerbation of the symptoms of reversible obstructive pulmonary disease.

Application of Treatment

The following illustrations are examples of the invention described herein. It is contemplated that combinations of aspects of specific embodiments or combinations of the specific embodiments themselves are within the scope of this disclosure.

Figure 2:
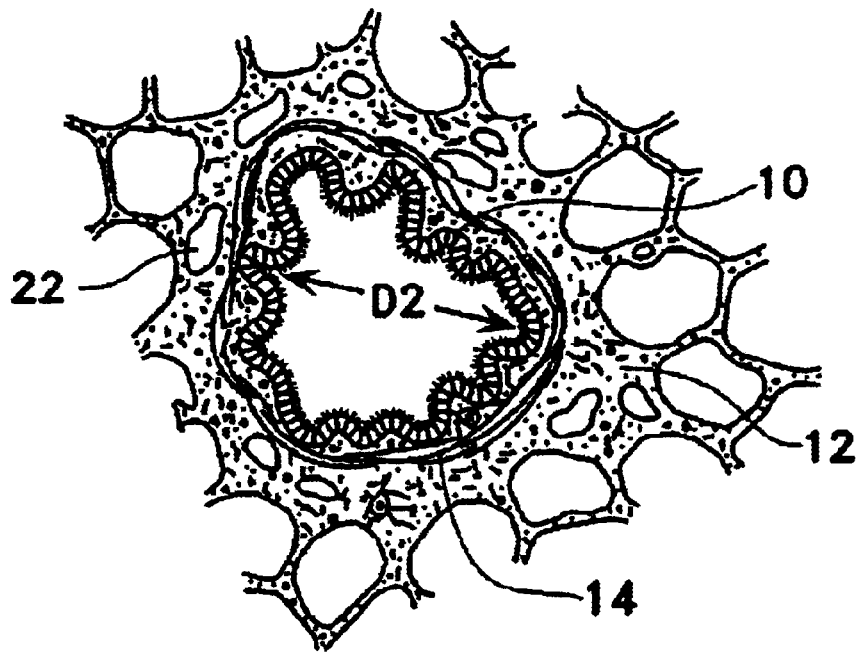
FIG. 2 shows a section through a bronchiole having an airway diameter smaller than that shown in FIG. 1.

FIGS. 1 and 2 illustrate cross sections of two different airways in a healthy patient. The airway of FIG. 1 is a medium sized bronchus having an airway diameter D1 of about 3 mm. FIG. 2 shows a section through a bronchiole having an airway diameter D2 of about 1.5 mm. Each airway includes a folded inner surface or epithelium 10 surrounded by stroma 12 and smooth muscle tissue 14. The larger airways including the bronchus shown in FIG. 1 also have mucous glands 16 and cartilage 18 surrounding the smooth muscle tissue 14. Nerve fibers 20 and blood vessels 22 also surround the airway.

Figure 3:
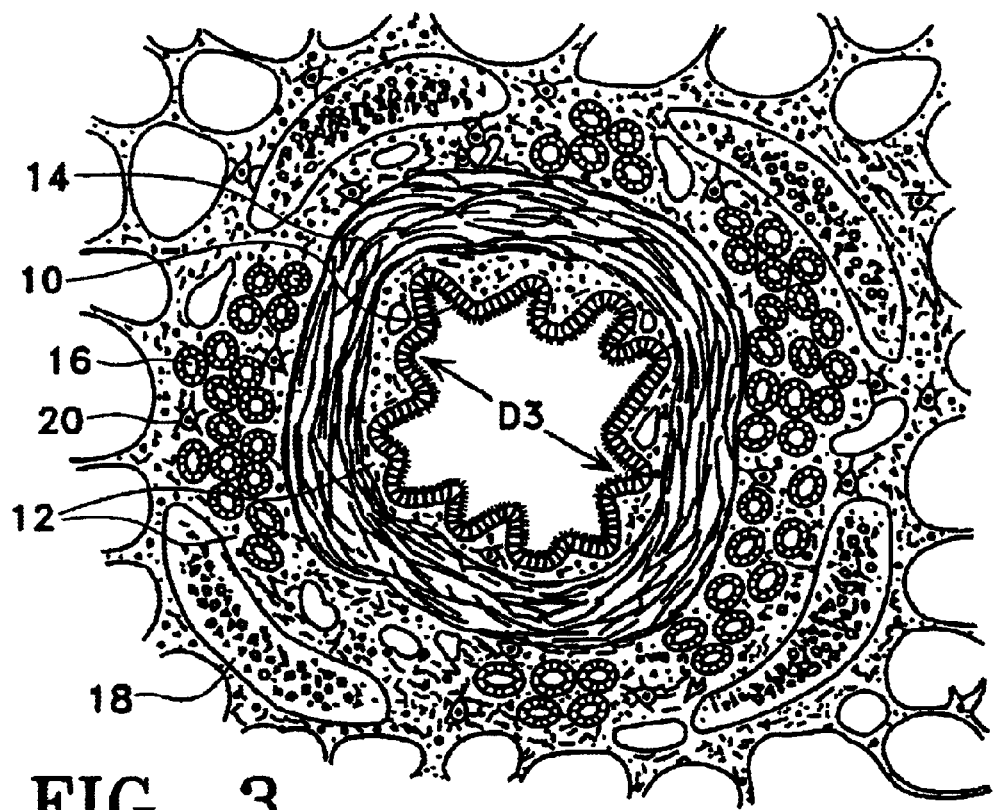
FIG. 3 illustrates the airway of FIG. 1 in which the smooth muscle 14 has hypertrophied and increased in thickness causing reduction of the airway diameter.

FIG. 3 illustrates the bronchus of FIG. 1 in which the smooth muscle 14 has hypertrophied and increased in thickness causing the airway diameter to be reduced from the diameter D1 to a diameter D3.

Figure 4:
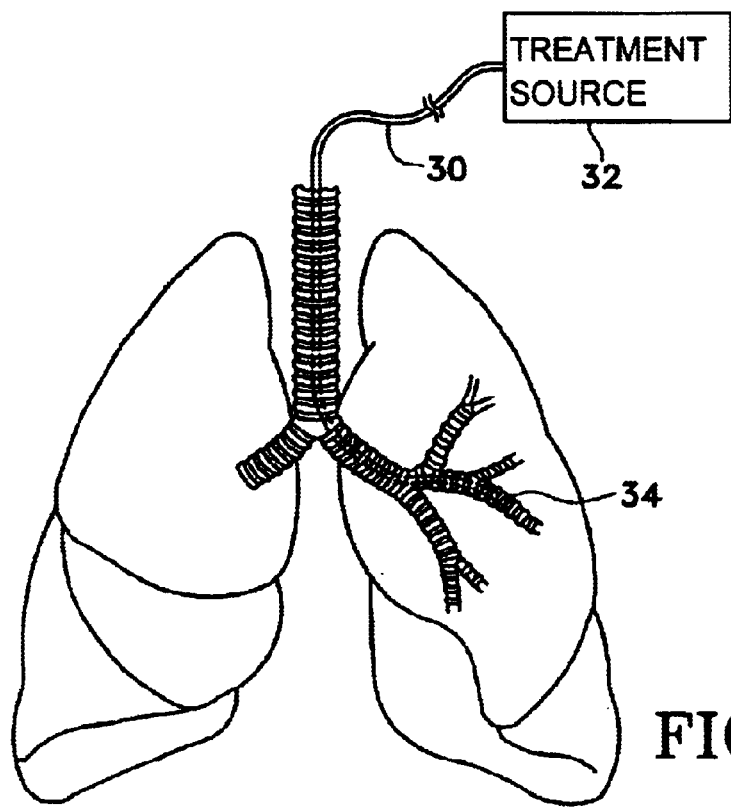
FIG. 4 is a schematic side view of the lungs being treated with a treatment device 30 as described herein.

FIG. 4 is a schematic side view of the lungs being treated with a treatment device 30 as described in the references incorporated by reference herein, as set forth below. The treatment device 30 is an elongated member for treating tissue at a treatment site 34 within a lung. The treatment device 30 may use a variety of processes to achieve a desired response. The treatment device 30 may use a modality of treatments as represented by the treatment source 32, including, but not limited to the following: chemical, radio frequency, radioactivity, heat, ultrasound, radiant, laser, microwave, or mechanical energy (such as in the form of cutting, punching, abrading, rubbing, or dilating). Although the invention discusses treatment of tissue at the surface it is also intended that the invention include treatment below an epithelial layer of the lung tissue.

An example of devices for use with the methods of this invention are found in the following U.S. patent applications: Ser. No. 09/095,323—Methods and Apparatus for Treating Smooth Muscles in the Walls of Body Conduits; Ser. No. 09/349,715—Method of Increasing Gas Exchange of a Lung; and Ser. No. 09/296,040—Devices for Modification of Airways By Transfer of Energy; Ser. No. 09/436, 455 Devices for Modification of Airways by Transfer of Energy. The entirety of each of the aforementioned applications is incorporated by reference herein.

The treatment of an airway with the treatment device may involve placing a visualization system such as an endoscope or bronchoscope into the airways. The treatment device is then inserted through or next to the bronchoscope or endoscope while visualizing the airways. Alternatively, the visualization system may be built directly into the treatment device using fiber optic imaging and lenses or a CCD and lens arranged at the distal portion of the treatment device. The treatment device may also be positioned using radiographic visualization such as fluoroscopy or other external visualization means. The treatment device which has been positioned with a distal end within an airway to be treated is energized so that energy is applied to the tissue of the airway walls in a desired pattern and intensity. The distal end of the treatment device may be moved through the airway in a uniform painting like motion to expose the entire length of an airway to be treated to the energy. The treatment device may be passed axially along the airway one or more times to achieve adequate treatment. The "painting-like" motion used to exposed the entire length of an airway to the energy may be performed by moving the entire treatment device from the proximal end either manually or by motor. Alternatively, segments, stripes, rings or other treatment patterns may be used.

According to one variation of the invention, the energy is transferred to or from an airway wall in the opening region of the airway, preferably within a length of approximately two times the airway diameter or less, and to wall regions of airways distal to bifurcations and side branches, preferably within a distance of approximately twice the airway diameter or less. The invention may also be used to treat long segments of un-bifurcated airway.

The invention includes a method of advancing a treatment device into a lung and treating the lung with the device to, at least, reduce the ability of the lung to produce at least one symptom of reversible obstructive pulmonary disease. It is contemplated that the treatment may reduce all of the symptoms of reversible obstructive disease. Alternatively, the treatment may be selected to address specific symptoms of the disease. It is also intended that the treatment of the lung may sufficiently reduce the symptoms of reversible obstructive pulmonary disease such that the patient is able to function as those free from the disease. Alternatively, the treatment may be such that the symptoms are reduced to allow the patient to more easily manage the disease. It is also intended that the effects of the treatment may be either long term or short term with repeating treatment necessary to suppress the symptoms.

The methods of the invention described herein may be performed while the lung is experiencing natural symptoms of reversible obstructive pulmonary disease. One such example is where an individual, experiencing an asthma attack, or acute exacerbation of asthma or COPD, undergoes treatment to improve the individual's ability to breath. In such a case, the treatment, called 'rescue,' seeks to provide immediate relief for the patient.

The method may also include the steps of locating one or more treatment sites within an airway of the lung, selecting one of the treatment sites from the locating step and treating at least one of the selected treatment sites. As mentioned above, these steps may be, but are not necessarily, performed while the lung is experiencing symptoms of reversible obstructive pulmonary disease.

The invention may further comprise the step of stimulating the lung to produce at least one artificially induced symptom of reversible obstructive pulmonary disease. For example, stimulation of the lung would preferably increase the resistance to airflow within the lung, constrict airways within the lung, inflame/irritate airway tissues, increase edema and/or increase the amount of mucus plugging of the airway. Stimulation of the lung may occur at any point during the procedure or before the procedure. For example, the lung may be stimulated either prior to or after, the step of locating a treatment site. If the lung is stimulated prior to the step of locating a treatment site, the reaction of the stimulated tissue within the lung may be useful in determining which locations are to be selected as treatment sites. The lung tissue or airway tissue within the lung may be stimulated by a variety of methods including but not limited to pharmacological stimulation, (e.g., histamine, methacholine, or other bronchoconstricting agents, etc.), electrical stimulation, mechanical stimulation, or any other stimuli causing obstructive pulmonary symptoms. For example, electrical stimulation may comprise exposing airway tissue to electrical field stimulation. An example of such parameters include 15 VDC, 0.5 ms pulses, 0.5–16 Hz, and 70 VDC, 2–3 ms pulses, 20 HZ.

The locating step described above may be performed using a non-invasive imaging technique, including but not limited to, a bronchogram, magnetic resonance imaging, computed tomography, radiography (e.g., x-ray), and ventilation perfusion scans.

The invention further includes the steps of testing the lung for at least one pre-treatment pulmonary function value prior to treating the lung with the device. After the lung is treated, the lung is re-tested for at least one post-treatment pulmonary function value. Naturally, the two pulmonary function values may be compared to estimate the effect of the treatment. The invention may also include treating additional sites in the lung after the re-testing step to at least reduce the effect, of at least one symptom of reversible obstructive pulmonary disease. The invention may also include stimulating the lung to produce at least one artificially induced symptom of reversible obstructive pulmonary disease. As mentioned above, the stimulation of the lung may occur at any point during, or prior to, the procedure. For example, stimulation of the lung may occur prior to the step of testing the lung for pre-treatment pulmonary values. In this case, the values would be determinative of pulmonary function values of a lung experiencing symptoms of reversible obstructive pulmonary disease. Accordingly, the objective is to treat the lung until acceptable pulmonary function values are obtained. One benefit of such a procedure is that the effect of the treatment on the patient is more readily observed as compared to the situation where a patient, having previously been treated, must wait for an attack of reversible obstructive pulmonary disease to determine the efficacy of the treatment.

Pulmonary function values are well known in the art. The following is an example of pulmonary function values that may be used. Other pulmonary function values, or combinations thereof, are intended to be within the scope of this invention. The values include, but are not limited to, FEV (forced expiratory volume), FVC (forced vital capacity), FEF (forced expiratory flow), Vmax (maximum flow), PEFR (peak expiratory flow rate), FRC (functional residual capacity), RV (residual volume), TLC (total lung capacity).

FEV measures the volume of air exhaled over a predetermined period of time by a forced expiration immediately after a full inspiration. FVC measures the total volume of air exhaled immediately after a full inspiration. Forced expiratory flow measures the volume of air exhaled during a FVC divided by the time in seconds. Vmax is the maximum flow measured during FVC. PEFR measures the maximum flow rate during a forced exhale starting from full inspiration. RV is the volume of air remaining in the lungs after a full expiration.

The locating step described above may also comprise identifying treatment sites within the airway being susceptible to a symptom of reversible obstructive pulmonary disease. For example, symptoms may include, but are not limited to, airway inflammation, airway constriction, excessive mucous secretion, or any other asthmatic symptom. Stimulation of the lung to produce symptoms of reversible obstructive pulmonary disease may assist in identifying ideal treatment sites.

As noted above, the method of the present invention may include stimulating the lung to produce at least one artificially induced symptom of reversible obstructive pulmonary disease and further include the step of evaluating the result of stimulation of the lung. For example, the evaluating step may include visually evaluating the effect of the stimulating step on the airway using a bronchoscope with a visualization system or by non-invasive imaging techniques, such as those describe herein. The evaluating step may include measuring pressure changes in the airway before and after the stimulating step. Pressure may be measured globally (e.g., within the entire lung), or locally (e.g., within a specific section of the lung such as an airway or alveolar sac.) Also, the evaluating step may comprise measuring the electrical properties of the tissue before and after the stimulating step. The invention may also include evaluating the results of the stimulating step by combining any of the methods previously mentioned. Also, the invention may further comprise the step of selecting at least one treatment parameter based upon the results of the evaluating step. Such treatment parameters may include, but are not limited to, duration of treatment, intensity of treatment, temperature, amount of tissue treated, depth of treatment, etc.

The method may also include the step of determining the effect of the treatment by visually observing lung, airway or other such tissue for blanching of the tissue. The term "blanching" is intended to include any physical change in tissue that is usually, but not necessarily, accompanied by a change in the color of the tissue. One example of such blanching is where the tissue turns to a whitish color after the treatment of application of energy.

The invention may also include the step of monitoring impedance across a treated area of tissue within the lung. Measuring impedance may be performed in cases of monopolar or bipolar energy delivery devices. Additionally, impedance may be monitored at more than one site within the lungs. The measuring of impedance may be, but is not necessarily, performed by the same electrodes used to deliver the energy treatment to the tissue. Furthermore, the invention includes adjusting the treatment parameters based upon the monitoring of the change in impedance after the treatment step. For example, as the energy treatment affects the properties of the treated tissue, measuring changes in impedance may provide information useful in adjusting treatment parameters to obtain a desired result.

Another aspect of the invention includes advancing a treatment device into the lung and treating lung tissue to at least reduce the ability of the lung to produce at least one symptom of reversible obstructive pulmonary disease and further comprising the step of sub-mucosal sensing of the treatment to the lung tissue. The sub-mucosal sensing may be invasive such as when using a probe equipped to monitor temperature, impedance, and/or blood flow. Or, the sub-mucosal sensing may be non-invasive in such cases as infra-red sensing.

The invention may also include using the treatment device to deposit radioactive substances at select treatment sites within the lung. The radioactive substances, including, but not limited to Iridium (e.g. $^{192}$Ir.) either treat the lung tissue over time or provide treatment upon being deposited.

The invention also includes scraping epithelial tissue from the wall of an airway within the lung prior to advancing a treatment device into the lung to treat the lung tissue. The removal of the epithelial tissue allows the device to treat the walls of an airway more effectively. The invention further comprises the step of depositing a substance on the scraped wall of the airway after the device treats the airway wall. The substance may include epithelial tissue, collagen, growth factors, or any other bio-compatible tissue or substance, which promotes healing, prevent infection, and/or assists in the clearing of mucus. Alternatively, the treatment may comprise the act of scraping epithelial tissue to induce yield the desired response.

The invention includes using the treating device to pre-treat the lung to at least reduce the ability of the lung to produce at least one symptom of reversible obstructive pulmonary disease prior to the treating step. At least one of the parameters of the pre-treating step may differ than one of the parameters of the treating step. Such parameters may include time, temperature, amount of tissue over which treatment is applied, amount of energy applied, depth of treatment, etc.

The invention may also include advancing the treatment device into the lung and treating the lung tissue in separate stages. One of the benefits of dividing the treating step into separate stages is that the healing load of the patient is lessened. Dividing of the treating step may be accomplished by treating different regions of the lung at different times. Or, the total number of treatment sites may be divided into a plurality of groups of treatment sites, where each group of treatment sites is treated at a different time. The amount of time between treatments may be chosen such that the healing load placed on the lungs is minimized.

The invention may also include advancing a treatment device into the lung, treating the lung with the device and sensing movement of the lung to reposition the treatment device in response to the movement. This sensing step accounts for the tidal motion of the lung during breathing cycles or other movement. Taking into account the tidal motion allows improved accuracy in repositioning of the device at a desired target.

The invention may also include the additional step of reducing or stabilizing the temperature of lung tissue near to a treatment site. This may be accomplished for example, by injecting a cold fluid into lung parenchyma or into the airway being treated, where the airway is proximal, distal, or circumferentially adjacent to the treatment site. The fluid may be sterile normal saline, or any other bio-compatible fluid. The fluid may be injected into treatment regions within the lung while other regions of the lung normally ventilated by gas. Or, the fluid may be oxygenated to eliminate the need for alternate ventilation of the lung. Upon achieving the desired reduction or stabilization of temperature the fluid may be removed from the lungs. In the case where a gas is used to reduce temperature, the gas may be removed from the lung or allowed to be naturally exhaled. One benefit of reducing or stabilizing the temperature of the lung may be to prevent excessive destruction of the tissue, or to prevent destruction of certain types of tissue such as the epithelium, or to reduce the systemic healing load upon the patient's lung.

Also contemplated as within the scope of the invention is the additional step of providing therapy to further reduce the effects of reversible obstructive pulmonary disease or which aids the healing process after such treatment. Some examples of therapy include, drug therapy, exercise therapy, and respiratory therapy. The invention further includes providing education on reversible obstructive pulmonary disease management techniques to further reduce the effects of the disease. For example, such techniques may be instruction on lifestyle changes, self-monitoring techniques to assess the state of the disease, and/or medication compliance education.

There may be occurrences where it is necessary to reverse the effects of the treatment described herein. Accordingly, the invention further includes a method for reversing a treatment to reduce the ability of the lung to produce at least one symptom of reversible obstructive pulmonary disease comprising the step of stimulating re-growth of smooth muscle tissue. The re-stimulation of the muscle may be accomplished by the use of electro-stimulation, exercising of the muscle and/or drug therapy.

The invention further includes methods of evaluating individuals having reversible obstructive pulmonary disease, or a symptom thereof, as a candidate for a procedure to reduce the ability of the individual's lung to produce at least one symptom of reversible obstructive pulmonary disease. The method comprises the steps of assessing the pulmonary condition of the individual, comparing the pulmonary condition to a corresponding pre-determined state, and evaluate the individual as a candidate based upon the comparison.

In assessing the pulmonary condition, the method may comprise the steps of performing pulmonary function tests on the individual to obtain a pulmonary function value which is compared to a predetermined value. Examples of pre-determined values are found above.

The method of evaluating may further include the step of determining how the individual's tissue will react to treatment allowing the treatment to be tailored to the expected tissue response.

The method of evaluating may further comprises the step of pulmonary function testing using a gas, a mixture of gases, or a composition of several mixtures of gases to ventilate the lung. The difference in properties of the gases may aid in the pulmonary function testing. For example, comparison of one or more pulmonary function test values that are obtained with the patient breathing gas mixtures of varying densities may help to diagnose lung function. Examples of such mixtures include air, at standard atmospheric conditions, and a mixture of helium and oxygen. Additional examples of pulmonary testing include tests that measure capability and evenness of ventilation given diffusion of special gas mixtures. Other examples of gases used in the described tests, include but are not limited to, nitrogen, carbon monoxide, carbon dioxide, and a range of inert gases.

The invention may also comprise the step of stimulating the lung to produce at least one artificially induced symptom of reversible obstructive pulmonary disease. Stimulating the symptoms of the disease in an individual allows the individual to be evaluated as the individual experiences the symptoms thereby allowing appropriate adjustment of the treatment.

The method of evaluating may also comprise the step of obtaining clinical information from the individual and accounting for the clinical information for treatment.

The method may further comprise the selection of a patient for treatment based upon a classification of the subtype of the patient's disease. For example, in asthma there are a number of ways to classify the disease state. One such method is the assessment of the severity of the disease. An example of a classification scheme by severity is found in the *NHLBI Expert Panel 2 Guidelines for the Diagnosis and Treatment of Asthma*. Another selection method may include selecting a patient by the type of trigger that induces the exacerbation. Such triggers may be classified further by comparing allergic versus non-allergic triggers. For instance, an exercise induced bronchospasm (EIB) is an example of a non-allergenic trigger. The allergic sub-type may be further classified according to specific triggers (e.g., dust mites, animal dander, etc.). Another classification of the allergic sub-type may be according to characteristic features of the immune system response such as levels of IgE (a class of antibodies that function in allergic reactions, also called immunoglobulin). Yet another classification of allergic sub-types may be according to the expression of genes controlling certain interleukins (e.g., IL-4, IL-5, etc.) which have been shown to play a key role in certain types of asthma.

The invention further comprises methods to determine the completion of the procedure and the effectiveness of the reduction in the lung's ability to produce at least one symptom of reversible obstructive pulmonary disease. This variation of the invention comprises assessing the pulmonary condition of the individual, comparing the pulmonary condition to a corresponding predetermined state, and evaluating the effectiveness of the procedure based on the comparison. The invention may also comprise the steps of performing pulmonary function tests on the individual to obtain at least one pulmonary function value, treating the lung to at least reduce the ability of the lung to produce at least one symptom of reversible obstructive pulmonary disease, performing a post-procedure pulmonary function tests on the individual to obtain at least one post pulmonary function value and comparing the two values.

This variation of the invention comprises obtaining clinical information, evaluating the clinical information with the results of the test to determine the effectiveness of the procedure. Furthermore, the variation may include stimulating the lung to produce a symptom of reversible obstructive pulmonary disease, assessing the pulmonary condition of the patient, then repeating the stimulation before the post-procedure pulmonary therapy. These steps allow comparison of the lung function when it is experiencing symptoms of reversible obstructive pulmonary disease, before and after the treatment, thereby allowing for an assessment of the improved efficiency of the lung during an attack of the disease.

The invention herein is described by examples and a desired way of practicing the invention is described. However, the invention as claimed herein is not limited to that specific description in any manner. Equivalence to the description as hereinafter claimed is considered to be within the scope of protection of this patent.

We claim as our invention:

1. A method for treating a lung having reversible obstructive pulmonary disease comprising the steps of:
   a) advancing a treatment instrument into the lung; and
   b) treating an airway wall of the lung with the instrument to at least reduce the ability of the lung to produce at least one reversible obstructive pulmonary disease symptom.

2. The method of claim 1 further comprising the steps of:
   a) locating one or more treatment sites within an airway of the lung;
   b) selecting at least one of the treatment sites located in said locating step; and
   c) wherein said treating step comprises treating the at least one treatment site selected in said selecting step.

3. The method of claim 2 wherein said steps are performed while the lung is experiencing at least one symptom of reversible obstructive pulmonary disease.

4. The method of claim 2 further comprising the step of stimulating the lung to produce at least one artificially induced symptom of reversible obstructive pulmonary disease.

5. The method of claim 4 wherein said stimulating step is performed prior to said locating step.

6. The method of claim 2 wherein said locating step is performed by a non-invasive imaging technique.

7. The method of claim 6 where the non-invasive imaging technique is selected from a group consisting of a bronchogram, magnetic resonance imaging, computed tomography, chest x-ray, and ventilation perfusion scans.

8. The method of claim 2 further comprising the steps of:
   a) testing the lung for at least one pre-treatment pulmonary function value prior to said treating step; and
   b) re-testing the lung for at least one post-treatment pulmonary function value subsequent to said treating step.

9. The method of claim 8 further comprising the step of treating additional sites in the lung after said re-testing step to at least reduce the effect of at least one symptom of reversible obstructive pulmonary disease in the lung until a desired posttreatment pulmonary function value is measured.

10. The method of claim 8 further comprising the step of stimulating the lung to produce at least one artificially induced symptom of reversible obstructive pulmonary disease.

11. The method of claim 8 wherein the pulmonary function value is selected from a group consisting of FEV (forced expiratory volume), FVC (forced vital capacity), FEF (forced expiratory flow), Vmax (maximum flow), PEFR (peak expiratory flow rate), FRC (functional residual capacity), RV (residual volume), TLC (total lung capacity), or a combination thereof.

12. The method of claim 2 wherein said locating step comprises identifying treatment sites within the airway being susceptible to a symptom selected from the group consisting of airway inflammation, airway constriction, excessive mucous secretion, and any other symptom of reversible obstructive pulmonary disease.

13. The method of claim 12 wherein said identifying step comprises stimulating the airway to produce at least one of the symptoms to identify the treatment sites.

14. The method of claim 13 where said stimulating step comprises pharmacologically stimulating the airway.

15. The method of claim 13 where said stimulating step comprises electrically stimulating the airway.

16. The method of claim 1 further comprising the step of stimulating the lung to produce at least one artificially induced symptom of reversible obstructive pulmonary disease.

17. The method of claim 16 wherein said stimulating step comprises electrically stimulating the lung.

18. The method of claim 16 wherein said stimulating step comprises pharmacologically stimulating the lung.

19. The method of claim 16 further comprising the step of evaluating the result of said stimulating step.

20. The method of claim 19 wherein said evaluating step comprises visually evaluating the effect of said stimulating step on the airway.

21. The method of claim 19 wherein said evaluating step comprises measuring the pressure change in the lung before and after said stimulating step.

22. The method of claim 21 wherein said measuring step comprises measuring a global pressure change in the lung.

23. The method of claim 21 wherein said measuring step comprises measuring a local pressure change in an airway.

24. The method of claim 19 wherein said evaluating step comprises measuring the resistance to airflow within the lungs before and after the stimulating step.

25. The method of claim 19 wherein said evaluating step comprises measuring the electrical properties of the tissue before and after the stimulating step.

26. The method of claim 19 further comprising the step of selecting at least one treatment parameter based upon said evaluating step.

27. The method of claim 26 wherein said stimulating step, evaluating step, and selecting at least one treatment parameter step are performed subsequent to said treating step.

28. The method of claim 1 wherein said steps are performed while the lung is experiencing an attack of reversible obstructive pulmonary disease.

29. The method of claim 1 wherein said treating step comprises treating at least airway tissue within the lung, the method further comprising the step of determining the effect of the treatment by visually observing the airway for blanching of airway tissue.

30. The method of claim 29 further comprising the step of adjusting at least one treatment parameter based upon said determining step.

31. The method of claim 1 wherein said treating step comprises treating at least airway tissue at a treatment site within the lung, the method further comprising the step of monitoring impedance in the tissue.

32. The method of claim 31 wherein said monitoring step includes monitoring impedance at one or more points within the lung.

33. The method of claim 31 further comprising the step of adjusting at least one treatment parameter based upon said monitoring step.

34. The method of claim 1 wherein said treating step comprises treating at least airway tissue at a treatment site within the lung, the method further comprising the step of sub-mucosal sensing step of the treatment to the lung tissue.

35. The method of claim 34 wherein the sensing comprises non-invasive sensing.

36. The method of claim 34 wherein the sensing step comprises invasive sensing.

37. The method of claim 36 wherein the invasive sensing comprises temperature, impedance or blood flow monitoring.

38. The method of claim 1 wherein said step of treating the lung comprises depositing a radioactive substance in at least one treatment site within the lung.

39. The method of claim 1 further comprising the steps of scraping epithelial tissue from a wall of an airway within the lung prior to said treating step.

40. The method of claim 39 further comprising the step of depositing a substance on the scraped wall of the airway after said treatment step.

41. The method of claim 40 wherein said substance is epithelial tissue, collagen, growth factors, or any other tissue from the patient's body.

42. The method of claim 1 wherein said treating step comprises treating an airway wall within the lung using a modality selected from the group consisting of mechanical, chemical, radio frequency, radioactive, heat, and ultrasound.

43. The method of claim 42 wherein said mechanical process comprises a process selected from the group consisting of cutting, punching, abrading, and rubbing.

44. The method of claim 1 further comprising the step of pre-treating the lung to at least reduce the ability of the lung to produce at least one symptom of reversible obstructive pulmonary disease prior to said treating step, wherein at least one parameter of said pre-treating step is lesser than at least one parameter of said treating step.

45. The method of claim 44 wherein a pre-treating step parameter of time or temperature is less than the treating step parameter of time or temperature.

46. The method of claim 1 wherein said treating step comprises separating said treating step into stages to reduce a healing load on the lung.

47. The method of claim 46 wherein said separating step comprises treating different regions of the lung at different times.

48. The method of claim 46 wherein said separating step comprises dividing a total number of treatment sites into at a plurality of groups of treatment sites, and treating each group at a different time.

49. The method of claim 1 wherein said treating step includes sensing movement of the lung and repositioning the treatment instrument in response to said sensing step.

50. The method of claim 1 further comprising the step of reducing or stabilizing the temperature of lung tissue adjacent to a treatment site.

51. The method of claim 50 wherein said reducing step comprises injecting a cold fluid into lung parenchyma, the method further comprising the step of removing the fluid from the lung.

52. The method of claim 1 wherein said treating step occurs below an epithelial layer of lung tissue.

53. The method of claim 1 further comprising the step of providing drug therapy to further reduce the effects of reversible obstructive pulmonary disease or aid in the healing process from said treatment.

54. The method of claim 1 further comprising the step of providing exercise therapy to further reduce the effects of reversible obstructive pulmonary disease.

55. The method of claim 1 further comprising the step of providing respiratory therapy to further reduce the effects of reversible obstructive pulmonary disease or aid in the healing process from said treatment.

56. The method of claim 1 further comprising the step of educating a patient on reversible obstructive pulmonary disease management techniques to reduce effects of reversible obstructive pulmonary disease.

57. A method for treating a lung having reversible obstructive pulmonary disorder was added to reduce the lung's ability to produce at least one of symptom of reversible obstructive pulmonary disease, the method comprising:

advancing a treatment instrument into the lung; and applying energy to an airway wall of an airway in the lung with the instrument.

58. The method of claim 57 further comprising the steps of:

locating one or more treatment sites within one or more airways of the lung;

selecting at least one of the treatment sites located in said locating step; and repeating the act of applying energy to the one or more treatment sites.

59. The method of claim 58 wherein said locating step is performed by a non-invasive imaging technique.

60. The method of claim 59 wherein said locating step is performed prior to advancing the treatment instrument into the lung.

61. The method of claim 59 where the non-invasive imaging technique is selected from a group consisting of a bronchogram, magnetic resonance imaging, computed tomography, chest x-ray, and ventilation perfusion scans.

62. The method of claim further comprising the steps of:

a) testing the lung for at least one pre-treatment pulmonary function value prior to said treating step; and b) re-testing the lung for at least one post-treatment pulmonary function value subsequent to the applying step.

63. The method of claim 62 wherein the pulmonary function value is selected from a group consisting of FEV (forced expiratory volume), FVC (forced vital capacity), FEF (forced expiratory flow), Vmax (maximum flow), PEFR (peak expiratory flow rate), FRC (functional residual capacity), RV (residual volume), TLC (total lung capacity), or a combination thereof.

64. The method of claim 58 wherein the locating step comprises identifying treatment sites within the Airway being susceptible to a symptom selected from the group consisting of airway inflammation, airway constriction, excessive mucous secretion, and any other symptom of reversible obstructive pulmonary disease.

65. The method of claim 57 wherein applying energy to the airway wall comprises heating the airway wall.

66. The method of claim 65 where heating the airway wall comprises applying radio frequency energy or heat to the airway wall.

67. The method of claim 65 where heating the wall comprises heating the wall to a pre-determined temperature.

68. The method of claim 65 where heating the airway wall comprises heating the airway wall in a pre-determined pattern.

69. The method of claim 68 where the predetermined pattern comprises a pattern selected from the group consisting of painting-like motion, segments, stripes, and rings.

70. The method of claim 57 wherein said treating step comprises separating said treating step into stages to reduce a healing load on the lung.

71. The method of claim 70 wherein said separating step comprises treating different regions of the lung at different times.

72. The method of claim 70 wherein said separating step comprises dividing a total number of treatment sites into at a plurality of groups of treatment sites, and treating each group at a different time.

73. The method of claim 57 further comprising the step of providing drug therapy to further reduce the effects of reversible obstructive pulmonary disease or aid in the healing process from said treatment.

74. The method of claim 57 further comprising the step of providing exercise therapy to further reduce the effects of reversible obstructive pulmonary disease.

75. The method of claim 57 further comprising the step of providing respiratory therapy to further reduce the effects of reversible obstructive pulmonary disease or aid in the healing process from said treatment.

76. The method of claim 57 where the symptom of reversible obstructive pulmonary disease comprises a symptom selected from the group consisting of contraction of airway tissue, inflammation of airway tissue, edema of airway tissue, and mucus plugging of the airway.

77. The method of claim 57 where the at least one of symptom of reversible obstructive pulmonary disease comprises symptoms of asthma.

* * * * *

UNITED STATES PATENT AND TRADEMARK OFFICE
CERTIFICATE OF CORRECTION

PATENT NO. : 6,634,363 B1 Page 1 of 1
DATED : October 21, 2003
INVENTOR(S) : Christopher J. Danek et al.

It is certified that error appears in the above-identified patent and that said Letters Patent is hereby corrected as shown below:

<u>Column 17,</u>
Line 67, please delete "was added".

Signed and Sealed this

Fourth Day of May, 2004

JON W. DUDAS
*Acting Director of the United States Patent and Trademark Office*